United States Patent [19]
Poulsen

[11] 4,062,361
[45] Dec. 13, 1977

[54] BILAMINAR OSTOMY SEALING DISC

[75] Inventor: Ib Finn Poulsen, Vaerloese, Denmark

[73] Assignee: Coloplast International A/S, Denmark

[21] Appl. No.: 593,252

[22] Filed: July 7, 1975

[30] Foreign Application Priority Data

July 8, 1974 Denmark .............................. 3660/74

[51] Int. Cl.² .............................................. A61F 5/44
[52] U.S. Cl. ...................................... 128/283; 428/65; 428/497; 428/521
[58] Field of Search ............... 128/283, 155, 156, 268, 128/1 R; 428/65, 64, 66, 500, 497, 521, 532

[56] References Cited
U.S. PATENT DOCUMENTS

| | | | |
|---|---|---|---|
| 2,563,597 | 8/1951 | Friedman | 128/283 |
| 2,593,210 | 4/1952 | Smith | 128/283 |
| 3,077,192 | 2/1963 | Berger | 128/283 |
| 3,249,109 | 5/1966 | Maeth et al. | 128/156 X |
| 3,302,647 | 2/1967 | Marsan | 128/283 |
| 3,339,546 | 9/1967 | Chen | 128/156 |
| 3,373,745 | 3/1968 | Benfield et al. | 128/283 |
| 3,612,053 | 10/1971 | Pratt | 128/283 |
| 3,640,741 | 2/1972 | Etes | 128/283 X |

*Primary Examiner*—Clifford D. Crowder
*Attorney, Agent, or Firm*—Anthony J. DeLaurentis

[57] ABSTRACT

An ostomy sealing disc adapted to fit around a stoma and forming a seal between the skin around the stoma and a drainage pouch, the sealing disc having an opening through which the digestive juices flow from the stoma into the drainage pouch and comprising a layer of a hydrocolloid and a layer of an elastomeric material, the two layers being firmly attached to each other.

6 Claims, 1 Drawing Figure

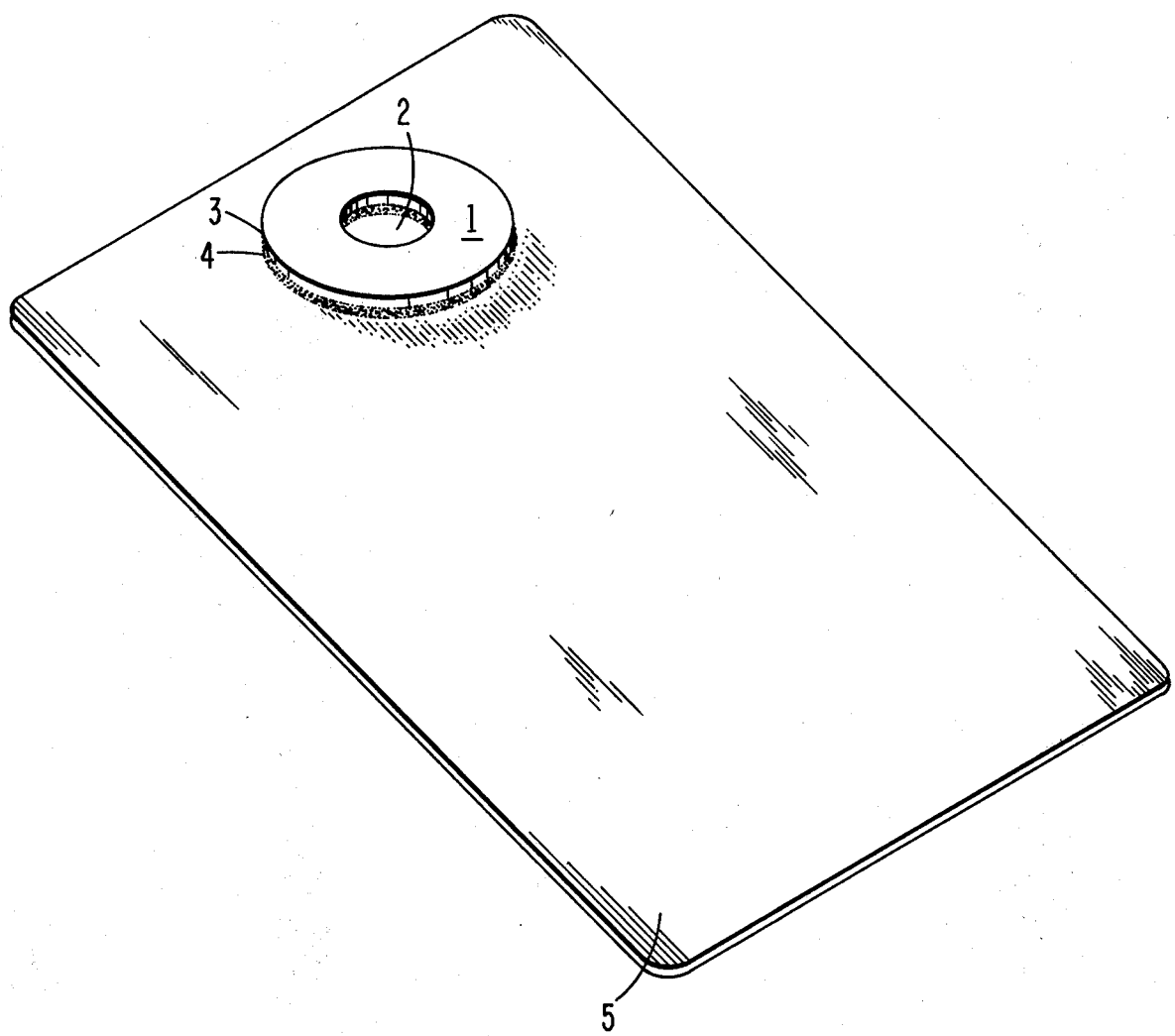

BILAMINAR OSTOMY SEALING DISC

The present invention relates to an ostomy sealing disc adapted to fit around a stoma and forming a seal between the skin around the stoma and a drainage pouch and a process for manufacturing said disc.

The stoma created, for example, at an Ileostomy, Colostomy or Ureterostomy is after the operation to be connected with a drainage pouch for collecting the discharge from the stoma. Usually, a pouch is attached to the patient's body so that the stoma projects into an opening of the pouch. To protect the stoma and to obtain a tenacious contact between the pouch and the skin a sealing disc with a central opening for receiving a stoma can be placed around the opening of the pouch. If the sealing disc is made of an elastic material, the opening of the disc for the stoma may appropriately be a little smaller than the outer diameter of the stoma, whereby a complete separation between the contents of the pouch and the human skin is achieved, and thus it is avoided that the skin-irritating liquid contained in the pouch touches the skin. To secure a tenacious adherence to the skin, also when the patient is moving, the side of the sealing disc facing the skin can be provided with an adhesive.

A sealing disc of this type is known from e.g. U.S. Pat. No. 3,612,053. By using a mono- or polylayer disc of an oil containing block copolymer, an advantageous flexibility is attained and sealing is always secured even if the patient is moving. The disc adheres to the skin by means of an adhesive that is activated by water, the secretion of sweat serving as an activator in the present case.

However, the sealing disc itself is not capable of absorbing essential amounts of sweat, whereby this will be entrapped in tiny cavities between the disc and the skin. First of all, this will have an irritating effect on the patient's skin, and furthermore — when more and more sweat is secreted — it will result in the fact that the disc detaches itself from the skin.

However, from U.S. Pat. No. 3,302,647 sealing discs are known which are capable of adhering to the skin and of absorbing the secretion of sweat, simultaneously, viz. sealing discs consisting of a gelled mixture of karaya powder and glycerol.

However, after having absorbed a certain amount of water these discs will be softened and thereby easily lose their shape and their capability of sealing. The amount of liquid absorbed as a consequence of the secretion of sweat will normally not produce such a softening effect, however, the side of such a disc facing the inner of the pouch absorbs water from the intestinal discharge from the stoma, and as this discharge contains much water, said side will rapidly absorb so much water that this side of the disc will be softened in a short time. In order to delay the softening of the entire karaya disc, it has to be relatively thick and thereby it looses its capability of following the movements of the human skin resulting in reduced sealing properties.

An object of the invention is to provide a sealing disc of the type described above but without the disadvantages of the hitherto known sealing discs.

Accordingly, an ostomy sealing disc is provided which is adapted to fit around a stoma and forming a seal between the skin around the stoma and a drainage pouch having an opening through which the digestive juices flow from the stoma and into the drainage pouch, and disc having elastic properties and on the side facing the skin being provided with an adhesive, and characterized in that the disc comprises two layers firmly attached to each other, one layer being composed by a hydrocolloid and the other layer being composed by an elastomeric material. The sealing disc or washer is illustrated in the accompanying drawing wherein numeral 1 represents a sealing disc having an opening 2 through which the digestive juices flow from a stoma (not shown) and into a drainage pouch 5. As discussed more fully hereinbelow, the sealing disc 1 is comprised of a layer 3 of a hydrocolloid material and a layer 4 of an elastomeric material which are firmly attached to each other.

Examples of hydrocolloid are polyvinylalcohol, powdered pectin, gelatine, carboxymethylcellulose, carbowax (polyethyleneglycole) with high molecular weight and carboxypolymethylene as well as mixtures thereof. However, the preferred hydrocolloid is karaya material, and therefore the invention will be explained in the following with reference to karaya material, although also other types of hydrocolloids may be employed for the sealing disc according to the invention.

By a sealing disc according to the invention a sealing is provided that is capable of absorbing sweat secretion without thereby being softened by the liquid contained in the pouch, said sealing providing high flexibility. As the layer of elastomeric material provides a sealing impermeable to liquids, the karaya layer only absorbs liquid from the human body and the layer can therefore be made rather thin with due consideration to the sweat secretion. Normally, a very thin and easy pliant karaya layer is capable of absorbing swear for an extended period of time without getting substantially softened.

Admittedly, by a simple lacquering of the one side of a karaya disc the disadvantageous absorption of the liquid from the pouch may be avoided, but such a disc will not offer a sufficient sealing effect, as explained in the following.

By combining the karaya material and the elastic material in a sealing disc according to the invention another advantage is obtained, namely that the karaya layer after a deformation is immediately affected by the elastomeric layer to regain its original shape. A sealing disc exclusively made of karaya material cannot, however, or only slowly regain its original shape after a deformation as it does not elastically change its shape when the defomation force ceases. As the outer diameter of the stoma normally is smallest at the root and largest at the open end of the stoma, the very mounting of the disc will deform same and thus complete sealing around the root of the stoma will be impossible.

The immediate regaining of the shape of the sealing disc according to the invention as a consequence of the force transmission between the elastomeric layer and the karaya layer is further intensified due to the thinness of the karaya layer. As the karaya layer only offers a limited resistance to the externally forced regaining of its original form, a sealing disc according to the invention shows almost the same flexibility as a similar disc of an elastomeric material. In a sealing disc of a karaya material, where a lacquer is applied to the one side for exclusion of liquid from the drainage pouch, the thin lacquer coating cannot, however, provide the disc with such strong resilient forces as those obtained in a disc according to the invention. Possibly, the lacquer coating may peel off at the deformation, and hereby the surface of the karaya layer will be exposed to the contents of the pouch.

A high flexibility is desirable not only due to immediate sealing purposes but also due to a continued adhering of the sealing disc to the skin, as repeated contact with and detachment from the skin reduces or dissolves the adhering-capability of the karaya layer and hereby also the sealing-capability. Besides, high flexibility means a greater degree of comfort for the patient, and also that the disc provides a better sealing around an irregular stoma. As mentioned, the employed karaya layer is advantageous due to its capability of absorbing water. Besides, the karaya layer can be tolerated by the skin, and the layer itself has an adhering effect. A possible residual thin film of karaya material from the detachment of the sealing disc is easily removed with a small amount of water. By using the karaya material one can thus avoid the use of adhesives, such as the water-activated adhesives — mentioned in U.S. Pat. No. 3,612,053 — which unintentionally, is easily inactivated by water, and which when detaching the disc leaves a remnant which is difficult to remove without damaging the skin.

The elastic modulus of the elastomeric material has to be chosen considering the following. An elastomeric layer with a small elastic modulus is very flexible but will easily undergo too heavy a deformation when exposed to an external force and can only with difficulty keep the karaya layer in its original shape. A layer with a large elastic modulus will rapidly after deformation try to regain its original shape, but is more rigid, and only with difficulty can the opening of the disc be adapted to the irregular circumference of the stoma without exposing same to too heavy a pressure; the difference between the opening of the disc and the outer diameter of the stoma is thus more critical. It will be appropriate to employ a comparatively thick elastic layer with a small elastic modulus rather than to employ a thin layer with a large elastic modulus, as in the former case the force effect towards the stoma is better dispersed over a larger area.

As far as the karaya layer is concerned, the thickness ought to be the smallest possible without sacrificing the water absorbing qualities, in this way maximum flexibility of the entire sealing disc is obtained. As karaya material it is suitable to use a gelled mixture of karaya powder and glycerol, preferably in the ratio of 1:2 to 2:1. Using such a mixture one is able to obtain an adequate conformability of the karaya material. A large glycerol content results in a soft karaya material whereas a small glycerol content produces a more rigid karaya layer.

As elastomeric material it is advisable to use an oil containing block copolymer, especially a styrene-isoprene or a stryrene-butadiene, the block copolymer and the oil in a ratio of 1:0.5 to 10. With such a block copolymer the elastic modules as desired for the elastomeric layer is attainable. With a large content of oil, e.g. paraffin oil, the material will be very soft whereas small amounts of oil result in a harder elastomeric layer.

The elastomeric material may further contain other substances, e.g. antioxidants and pigments.

As mentioned, sealing discs according to the invention must possess high flexibility, however, without changing shape too much when exposed to an external force. According to an embodiment of the invention, this is achieved by a sealing disc where the karaya disc is 0.5 to 3 mm thick, preferably 0.1 to 1.5 mm, and the disc of the elastomeric material is 1 to 5 mm thick, preferably 1 to 2 mm.

It has become apparent that the ratio between the thickness of the layer made of elastomeric material and the thickness of the layer of karaya material should be 1.5:1 in order to secure a sufficiently elastic force transmission from the elastomeric layer to the karaya layer and a satisfactory sealing effect of the disc.

The area of the side of the sealing disc placed towards the skin is dependent on the purpose of application and on the attachment to the body of the pouch. Although a larger immediate adhering surface is obtained when using large areas, it cannot be taken for granted that the adhesive power of the dic when used in larger than that of a small disc. In fact, a large disc will not be able to follow the movements of the skin to the same extent as would a small disc. According to the invention, it is appropriate that the diameter of a disc is from 3 to 10 cm.

According to the invention, when applying a sealing disc to the skin, a disc with an opening diameter that is somewhat smaller than the diameter of the stoma at the root is preferably chosen. The sealing disc is then placed on the body around the stoma by expanding the opening of the disc with the hand, then the disc is pulled over the stoma to be applied to the skin, and thereafter the disc will contract so that the opening seals completely around the stoma. Before the attachment the karaya layer may be moistened with water on the surface that is to be in tenacious contact with the skin, thus an immediate adhering is attained. Then the drainage pouch is placed with the opening towards the sealing disc, and the pouch is attached to the body by means of an adhesive and/or straps. As the elastomeric layer possesses a slight adhesiveness, it is not necessary directly to connect the sealing disc with the opening area of the pouch by means of an adhesive, although, of course, it is possible to provide a firm connection by means of an adhesive. During application, the pouch is pressed against the sealing disc either by means of a supporting sheet — a so-called faceplate — provided with straps to be attached around the body, or by means of an adhesive layer placed on the outside of the pouch adhering to the body outside the area covered by the sealing disc and possibly this adhesive also adheres the sealing disc to the pouch.

After a certain amount of sweating the karaya layer gets unacceptably soft and then has to be discarded. It is convenient to change the sealing disc at the same time as the emptying and the cleaning of the pouch take place. In this way, the disc will at any time fulfill its purposes. However, a change may also be made when the karaya layer has become unusable.

In the above, the sealing disc according to the invention and the drainage pouch are described as two separate units, but from the factory they can also be formed as one unit.

A requirement of the applicability of a sealing disc according to the invention is a firm connection between the karaya layer and the elastomeric layer even in the case of intensive deformation of the sealing disc. By means of a special process it is possible to obtain an extremely strong joint between the two layers without the use of adhesive between these. This process, also being the object of the invention, is characterized in that an even layer of karaya powder is applied on the one side of a layer of elastomeric material, then a liquid mixture of non-gelled karaya material is applied in the desired thickness and gelled, whereupon — possibly after application of a protection layer on the karaya layer — the formed multi layer product is punched or cut out to discs of the desired shape and size.

In a sealing disc thus produced, the two layers will, while the sealing disc is being used, stay firmly connected over their entire contact surfaces, which cannot be guaranteed in the case of a sealing disc, in which the karaya layer is simply gelled on an elastomeric layer, or in which the karaya layer by means of an adhesive is attached to the elastomeric layer.

The liquid mixture of the karaya material can, e.g. be a mixture of karaya powder and glycerole in the ratio of 1:2 to 2:1 especially 1:1.

The gelling of the mixture may be accelerated by heating, e.g. at a temperature of 80° - 150° C.

As protection layer it is advisable to use a piece of paper coated with e.g. silicone or paraffin wax, or a polyethylenefilm. This cover protects the surface of the karaya layer against impurities from the surroundings and prevents drying of the karaya layer. By using a sealing disc as per the invention the cover film is easily removable from the surface of the karaya layer without damaging same.

The process of the invention is illustrated in the following example.

EXAMPLE

A siliconized piece of paper is coated with a 1.5 mm thick elastomeric layer of a melted mass of an elastomeric mixture (temperature about 160° C) with the following composition:

|  | parts by weight |
| --- | --- |
| Blockcopolymer styrene-isoprene ('Cariflex TR1107') | 125 |
| Liquid paraffin | 175 |
| Antioxidant | 5 |
| Pigment (Titanium dioxide) | 10 |

Immediately thereafter the elastomeric layer is coated with a thin layer of karaya powder on one entire side, and thereafter a 1 mm thick layer of a non-gelled mixture of karaya powder and glycerole (1:1) is applied.

At a speed of 1 m/minute the produced multi-layer product is passed under IR-lamps whereby the mixture gels. The free karaya surface is covered with a siliconized piece of paper, and the desired sealing discs are punched out of the multi-layer material thus produced.

What we claim is:

1. An ostomy sealing disc adapted to fit around a stoma and forming a seal between the skin around the stoma and a drainage pouch having an opening through which the digestive juices flow from the stoma and into the drainage pouch, said disc comprising a first layer of a hydrocolloid material and a second layer of an elastomeric material, said layers being firmly attached to each other.

2. A sealing disc according to claim 1, characterized in that the hydrocolloid material is a karaya material.

3. A sealing disc according to claim 2, characterized in that the karaya material is a gelled mixture of karaya powder and glycerol in the ratio of 1:2 to 2:1, and that the elastomeric material is an oil containing block copolymer selected from the group consisting of styrene-isoprene and styrene-butadiene copolymer, the block copolymer and the oil being present in the ratio of 1:0.5–10.

4. A sealing disc according to claim 3, characterized in that the layer of karaya material is from 0.5 to 3 mm thick, and that the layer of elastomeric material is from 1 to 5 mm thick.

5. A sealing disc according to claim 3, characterized in that the ratio between the thickness of the layer of elastomeric material and the thickness of the layer of karaya material is 1.5:1.

6. An ileostomy, colostomy or ureterostomy pouch adapted to fit around a stoma and having an opening through which a discharge from the stoma may pass into the pouch, said pouch comprising a sealing disc attached to said pouch for forming a seal with respect to the skin around the stoma, said disc comprising a first layer of a hydrocolloid material and a second layer of an elastomeric material, said layer being firmly attached to each other and said elastomeric layer being attached to said pouch.

* * * * *